United States Patent [19]

Muramatsu et al.

[11] Patent Number: 4,552,754

[45] Date of Patent: Nov. 12, 1985

[54] HAIR COSMETIC COMPOSITION

[75] Inventors: Kazuhiro Muramatsu, Yachiyo; Yuuzi Watari, Chiba; Masaru Tajima, Tokyo; Isamu Nakaju, Chiba, all of Japan

[73] Assignee: Lion Corporation, Tokyo, Japan

[21] Appl. No.: 482,574

[22] Filed: Apr. 6, 1983

[30] Foreign Application Priority Data

Apr. 15, 1982 [JP]  Japan ................... 57-62957

[51] Int. Cl.$^4$ .................. A61K 7/06; A61K 7/08
[52] U.S. Cl. ................. 424/70; 424/DIG. 1; 514/345; 514/772; 514/786; 514/784
[58] Field of Search ............ 424/70, 263, DIG. 1, 424/358, 365

[56] References Cited

U.S. PATENT DOCUMENTS

| | | | |
|---|---|---|---|
| 2,540,218 | 2/1951 | Shaw | 424/263 |
| 2,742,393 | 4/1956 | Bernstein et al. | 424/308 X |
| 2,748,142 | 5/1956 | Clauson-Kaas et al. | 424/263 |
| 3,236,733 | 2/1960 | Karsten et al. | 424/70 |
| 3,644,626 | 2/1972 | Witzel | 424/263 |
| 3,655,897 | 4/1972 | Witzel | 424/263 |
| 3,883,545 | 5/1975 | Lohaus et al. | 260/297 Z |
| 3,968,118 | 7/1976 | Lohaus et al. | 260/297 Z |
| 3,972,888 | 8/1976 | Lohaus et al. | 260/297 Z |
| 4,293,542 | 10/1981 | Lang et al. | 424/63 |
| 4,307,089 | 12/1981 | Melloh | 424/245 |

FOREIGN PATENT DOCUMENTS

| | | | |
|---|---|---|---|
| 2416556 | 10/1975 | Fed. Rep. of Germany | 424/358 |
| 14-21760 | 3/1939 | Japan | 424/195 |
| 49-6657 | 2/1974 | Japan | 424/358 |
| 50-23841 | 8/1975 | Japan | 424/70 |
| 51-98340 | 8/1976 | Japan | 424/358 |
| 0055307 | 5/1981 | Japan | 424/358 |
| 0071020 | 6/1981 | Japan | 424/358 |

*Primary Examiner*—Dale R. Ore
*Attorney, Agent, or Firm*—Bacon & Thomas

[57] ABSTRACT

A hair cosmetic composition having a strong gelation-preventive property comprising about 0.1 to about 10% by weight of a certain quaternary ammonium salt, about 0.05 to about 3.0% by weight of a certain 1-hydroxy-2-pyridone salt, about 0.05 to about 20% by weight of a certain polyol derivative, and a cosmetically acceptable carrier.

11 Claims, No Drawings

HAIR COSMETIC COMPOSITION

BACKGROUND OF THE INVENTION

I. Field of the Invention

The present invention relates to a hair cosmetic composition and, more particularly, to a hair cosmetic composition having a strong gelation-preventive property.

II. Description of the Prior Art

A hair cosmetic composition such as a hair rinse composition, a hair treatment composition, and a hair cream composition conventionally contains an anionic polymer of an acrylic acid series, a carboxylic acid series or the like, or a nonionic polymer of a cellulose series, a pyrrolidone series or the like, in order to prevent gelation of the hair cosmetic composition. Such a polymer, however, does not have a sufficiently strong gelation-preventive effect. Furthermore, when such hair compositions are left on the hair, films of the polymer are formed thereon. As a result, individual hairs become so stiff that hair scaling or flaking may occur when the hair is combed.

In order to prevent the gelation of hair cosmetic composition, it has been proposed to use a highly hydrophilic nonionic surface-active agent or surfactant. When a highly hydrophilic nonionic surface-active agent is added in an amount sufficient to impart a gelation-preventive effect, a so-called "conditioning effect" of a hair cosmetic composition, which renders the hair soft and pliable and allows smooth and easy combing, is reduced.

SUMMARY OF THE INVENTION

It is, therefore, an object of the present invention to provide a hair cosmetic composition providing a strong conditioning effect and allowing substantially no gelation.

This object and other objects of the present invention can be accomplished by a hair cosmetic composition comprising:

(A) at least one quaternary ammonium salt represented by general formula (I) in an amount ranging from about 0.1 to about 10% by weight;

(B) at least one 1-hydroxy-2-pyridone salt represented by general formula (II) in an amount ranging from about 0.05 to about 3.0% by weight;

(C) at least one polyol derivative represented by general formula (III), (IV) or (V) in an amount ranging from about 0.05 to about 20% by weight; and (D) a cosmetically acceptable carrier; wherein said general formula (I) is:

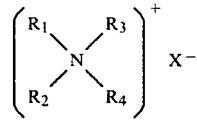

(where $R_1$ is a $C_{10}$–$C_{24}$ alkyl group, a $C_{10}$–$C_{24}$ hydroxyalkyl group, or a group having the formula $R'(OCH_2CH_2)_{1-10}$ (where $R'$ is a $C_{10}$–$C_{24}$ alkyl group or a $C_{10}$–$C_{24}$ hydroxyalkyl group); $R_2$ is a $C_{10}$–$C_{24}$ alkyl group, a $C_{10}$–$C_{24}$ hydroxyalkyl group, benzyl group, a group having the formula $R''(OCH_2CH_2)_{1-10}$ (where $R''$ is a $C_{10}$–$C_{24}$ alkyl group or a $C_{10}$–$C_{24}$ hydroxyalkyl group), a $C_1$–$C_3$ alkyl group, or a group having the formula

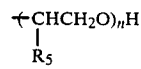

(where $n$ is an integer from 1 to 5 and $R_5$ is hydrogen atom or methyl group);

$R_3$ and $R_4$ are independently a $C_1$–$C_3$ alkyl group or a group having the formula

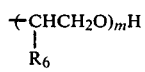

(where $m$ is an integer from 1 to 5 and $R_6$ is hydrogen atom or methyl group); and X is a halogen atom or a $C_1$–$C_2$ alkyl sulfate group); said general formula (II) is:

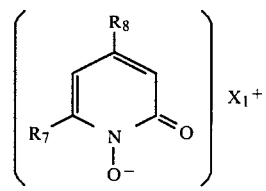

(where $R_7$ is a $C_1$–$C_{17}$ alkyl group, a $C_2$–$C_{17}$ alkenyl group, a $C_5$–$C_8$ cycloalkyl group, a $C_7$–$C_9$ bicycloalkyl group, a $C_1$–$C_4$ cycloalkyl-alkyl group (where the cycloalkyl residue may optionally be substituted by a $C_1$–$C_4$ alkyl group), an aryl group, an aralkyl group containing a $C_1$–$C_4$ alkyl group, an arylalkenyl group containing a $C_2$–$C_4$ alkenyl group, an aryloxyalkyl group containing a $C_1$–$C_4$ alkyl group, an arylmercaptoalkyl group containing a $C_1$–$C_4$ alkyl group, a benzhydryl group, a phenylsulfonylalkyl group containing a $C_1$–$C_4$ alkyl group, a furyl group, or a furylalkenyl group containing a $C_2$–$C_4$ alkenyl group, provided that said aryl residue may optionally be substituted by a $C_1$–$C_4$ alkyl group, a $C_1$–$C_4$ alkoxy group, nitro group, cyano group or a halogen atom;

$R_8$ is hydrogen atom, a $C_1$–$C_4$ alkyl group, a $C_2$–$C_4$ alkenyl group, a $C_2$–$C_4$ alkynyl group, a halogen atom, a phenyl group or a benzyl group; and $X_1$ is an organic base, an alkali metal, an alkaline earth metal, ammonium group, or a cation of +2 to +4 valence;

said general formula (III) is:

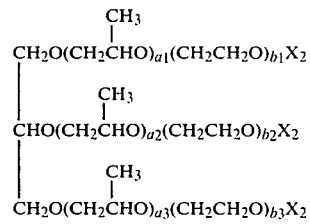

(where at least one of $X_2$ is a pyrrolidone carboxylic acid residue and the remaining $X_2$ are each independently hydrogen atom, a higher aliphatic acid residue or a higher hydroxylaliphatic acid residue;

$a_1$, $a_2$, $a_3$, $b_1$, $b_2$ and $b_3$ are same or different integers and a total sum of $a_1+a_2+a_3+b_1+b_2+b_3$ is an integer between 10 and 70);

said general formula (IV) is:

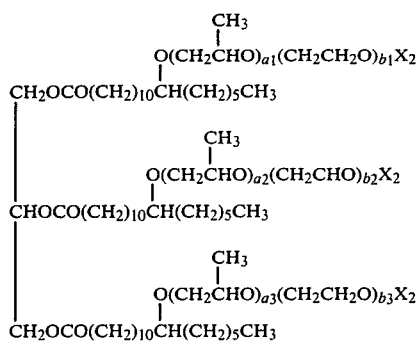

(where $X_2$, $a_1$, $a_2$, $a_3$, $b_1$, $b_2$ and $b_3$ have the same meanings as in formula (III)); and said general formula (V) is:

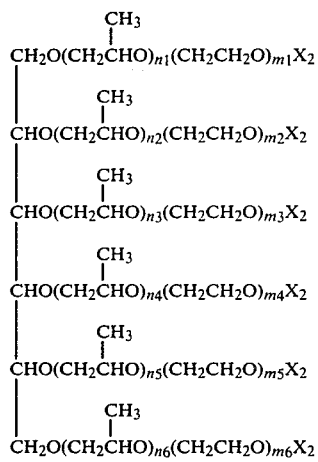

(where $X_2$ has the same meaning as in formula (III) above;

$m_1$, $m_2$, $m_3$, $m_4$, $m_5$, $m_6$, $n_1$, $n_2$, $n_3$, $n_4$, $n_5$ and $n_6$ are same or different integers and a total sum of $m_1+m_2+m_3+m_4+m_5+m_6+n_1+n_2+n_3+n_4+n_5+n_6$ is an integer between 10 and 100).

The hair cosmetic composition according to the present invention has a strong conditioning effect and allows substantially no gelation.

DETAILED DESCRIPTION OF THE PREFERRED EMBODIMENTS

The quaternary ammonium salt represented by general formula (I) is a first essential ingredient required for the present invention and may include a mono(long-chain)alkyl quaternary ammonium salt, a benzyl quaternary ammonium salt and a di(long-chain)alkyl quaternary ammonium salt. The number of carbon atoms of the long-chain alkyl residue ranges from 10 to 24, and preferably from 12 to 22. The number of carbon atoms of the long-chain alkyl residue is a highly significant factor. When the carbon atom number is below 10, the hair is not rendered as soft and pliable. When the carbon atom number is over 24, the hair is rendered stiff and hard. Where the alkyl group has a carbon atom number within the above-mentioned range, the resulting hair cosmetic composition is provided with an appropriately hydrophobic property, resulting in compatibility with hair. It also has a superior effect in rendering hair soft and pliable and causes an appropriate degree of moisture retention.

The long-chain alkyl groups defined hereinabove may have a hydroxyl group as a substituent. Thus, the above-mentioned quaternary ammonium salt may include a mono-$C_{10}$-$C_{24}$, preferably $C_{12}$-$C_{22}$ hydroxyalkyl quaternary ammonium salt and a di-$C_{10}$-$C_{24}$, preferably $C_{12}$-$C_{22}$ hydroxyalkyl quaternary ammonium salt.

The long-chain alkyl group and the long-chain hydroxyalkyl group may further contain from one to 10 ethylene oxide units. In other words, the quaternary ammonium salt may contain one or two of groups represented by the formula $R(OCH_2CH)_{1-10}$ (where R is a $C_{10}$-$C_{24}$, preferably $C_{12}$-$C_{22}$ alkyl group or a $C_{10}$-$C_{24}$, preferably $C_{12}$-$C_{22}$ hydroxyalkyl group).

The other groups which may be linked to the nitrogen atom of the quaternary ammonium salt is a $C_1$-$C_3$, preferably $C_1$-$C_2$ alkyl group or a group represented by the formula

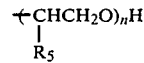

(where n is an integer from 1 to 5 and $R_5$ is hydrogen atom or methyl group).

The symbol X constituting an anion of the quaternary ammonium salt is a halogen atom or a $C_1$-$C_2$ alkyl sulfate group. Where the symbol X is a halogen atom or a $C_1$-$C_2$ alkylsulfate group, the resulting hair cosmetic composition has appropriate hydrophobic and water-retention properties.

Preferred examples of the quaternary ammonium salts may be dimethyldistearylammonium chloride, stearyltrimethylammonium chloride, dimethylstearylammonium chloride, behenyltriethanolammonium bromide.

The quaternary ammonium salts to be used here are well known in the field pertinent to the present invention, and may be readily manufactured by those having ordinary skills in the art pertinent thereto.

The hair cosmetic composition according to the present invention contains the quaternary ammonium salt in an amount ranging from about 0.1 to about 10% by weight. Where the amount thereof is below about 0.1% by weight, the conditioning effect cannot be provided. Where its amount exceeds about 10% by weight, the treated hair becomes heavy.

The second essential ingredient of the hair cosmetic composition according to the present invention is a 1-hydroxy-2-pyridone salt represented by formula (II). The preferred 1-hydroxy-2-pyridone salt is an organic amine salt of 1-hydroxy-2-pyridones such as 1-hydroxy-2-pyridone, 1-hydroxy-4-methyl-2-pyridone, 1-hydroxy-6-methyl-2-pyridone, 1-hydroxy-4,6-dimethyl-2-pyridone, 1-hydroxy-4-methyl-6-heptyl-2-pyridone, 1-hydroxy-4-methyl-6-(1-ethylpentyl)-2-pyridone, 1-hydroxy-4-methyl-6-(2,4,4-trimethylpentyl)-2-pyridone, 1-hydroxy-4-methyl-6-undecyl-2-pyridone, 1-hydroxy-4-methyl-6-propenyl-2-pyridone, 1-hydroxy-4-methyl-6-octenyl-2-pyridone, 1-hydroxy-4-methyl-6-(2,2-dibutylvinyl)-2-pyridone, 1-hydroxy-4-methyl-6-(dicyclohexenylidenemethyl)-2-pyridone, 1-hydroxy-4-methyl-6-cyclohexyl-2-pyridone, 1-hydroxy-4-methyl-6-(methylcyclohexyl)-2-pyridone, 1-hydroxy-4-methyl-6-(2-bicyclo[2,2,1]heptyl)-2-pyridone, 1-hydroxy-4-methyl-6-[2-(dimethylcyclohexyl)propyl]-2-pyridone, 1-hydroxy-4-methyl-6-(4-methylphenyl)-2-pyridone,
1-hydroxy-4-methyl-6-(3-methylphenyl)-2-pyridone,
1-hydroxy-4-methyl-6-(4-tertiary-butylphenyl)-2-pyridone, 1-hydroxy-4-methyl-6-(3-methyl-4-chlorophenyl)-2-pyridone, 1-hydroxy-4-methyl-6-(3,5-dichlorophenyl)-2-pyridone, 1-hydroxy-4-methyl-6-(3-bromo-4-chlorophenyl)-2-pyridone, 1-hydroxy-4-methyl-6-(4-methoxystyryl)-2-pyridone, 1-hydroxy-4-methyl-6-[1-(4-nitrophenoxy)butyl]-2-pyridone, 1-hydroxy-4-methyl-6-(4-cyanophenoxymethyl)-2-pyridone, 1-hydroxy-4-methyl-6-(phenylsulfonylmethyl)-2-pyridone, 1-hydroxy-4-methyl-6-[1-(4-chlorophenylsulfonyl)butyl]-2-pyridone, 1-hydroxy-4-methyl-6-benzyl-2-pyridone, 1-hydroxy-4-methyl-6-(2,4-dimethylbenzyl)-2-pyridone, 1-hydroxy-4-methyl-6-(tertiary-butylbenzyl)-2-pyridone, 1-hydroxy-4-methyl-6-(2-chlorobenzyl)-2-pyridone, 1-hydroxy-4-methyl-6-(4-chlorobenzyl)-2-pyridone, 1-hydroxy-4-methyl-6-(2,5-dichlorobenzyl)-2-pyridone, 1-hydroxy-4-methyl-6-(4-bromobenzyl)-2-pyridone, 1-hydroxy-4-methyl-6-(phenoxymethyl)-2-pyridone, 1-hydroxy-4-methyl-6-(3-methylphenoxymethyl)-2-pyridone, 1-hydroxy-4-methyl-6-(4-secondary-butylphenoxymethyl)-2-pyridone, 1-hydroxy-4-methyl-6-(2,4,5-trichlorophenoxymethyl)-2-pyridone, 1-hydroxy-4-methyl-6-(4-bromophenoxymethyl)-2-pyridone, 1-hydroxy-4-methyl-6-(4-chlorophenylmercaptomethyl)-2-pyridone, 1-hydroxy-4-methyl-6-(4-methylphenylmercaptomethyl)-2-pyridone, 1-hydroxy-4-methyl-6-(2-naphthyl)-2-pyridone, 1-hydroxy-4-methyl-6-benzhydryl-2-pyridone, 1-hydroxy-4-methyl-6-furyl-2-pyridone, 1-hydroxy-4-methyl-6-(furylvinyl)-2-pyridone, 1-hydroxy-4-methyl-6-styryl-2-pyridone, 1-hydroxy-4-methyl-6-(phenylbutadienyl)-2-pyridone, 1-hydroxy-4-phenyl-6-methyl-2-pyridone and 1-hydroxy-4,6-diphenyl-2-pyridone.

Preferred examples of the organic amines constituting the 1-hydroxy-2-pyridone salts are ethanolamine, diethanolamine, N-ethylethanolamine, N-methyl diethanolamine, triethanolamine, diethylaminoethanol, 2-amino-2-methyl-n-propanol, dimethylaminopropanol, 2-amino-2-methyl-propanediol, triisopropanolamine, ethylenediamine, hexamethylenediamine, morpholine, biperidine, cyclohexylamine, tributylamine, dodecylamine, N,N-dimethyldodecylamine, stearylamine, oleylamine, benzylamine, dibenzylamine, N-ethylbenzylamine, dimethylstearylamine, N-methylmorpholine, N-methylpiperazine, 4-methylcyclohexylamine and N-hydroxyethylmorpholine.

The hair cosmetic composition according to the present invention contains the 1-hydroxy-2-pyridone salt in an amount ranging from about 0.05 to about 3% by weight, and preferably from about 0.1 to about 2% by weight. Where the amount thereof is below about 0.05% by weight, the hair tips become dry and split. Where the amount thereof is in excess of about 3% by weight, hairs are rendered sticky.

The 1-hydroxy-2-pyridone salts per se are known and may be prepared, for example, by processes described in U.S. Pat. No. 2,540,218 and DOS No. 1,795,270.

The third essential ingredient of the hair cosmetic composition according to the present invention is the polyol derivative of formula (III), (IV) or (V). In formulas (III), (IV) and (V), at least one of the symbols $X_2$ is a residue of a pyrrolidone carboxylic acid, and the remainder thereof are independently hydrogen atom or a residue of a higher aliphatic acid or of a higher hydroxyaliphatic acid. Specific examples of the higher aliphatic acids supplying the higher aliphatic acid residues may include a higher straight chain saturated aliphatic acid such as lauric acid, myristic acid, palmitic acid, stearic acid, arachidic acid, behenic acid, cerotic acid or the like; a higher straight chain unsaturated aliphatic acid such as zoomaric acid, petroselinic acid, oleic acid, erucic acid, linolic acid, linoleic acid or the like; and a higher branched chain saturated aliphatic acid such as isostearic acid. Specific examples of the higher hydroxy saturated aliphatic acids supplying the residues of the higher hydroxy aliphatic acids may include a higher hydroxy saturated aliphatic acid such as 1,2-dihydroxystearic acid or the like and a higher hydroxy unsaturated aliphatic acid such as ricinoleic acid or the like.

In formula (III) and (IV), each of $a_1$, $a_2$, $a_3$, $b_1$, $b_2$ and $b_3$ is an integer and a total of $a_1+a_2+a_3+b_1+b_2+b_3$ is in the range between 10 and 70. Where the total is below 10, a hydrophilic property of the hair cosmetic composition is rendered so poor that no gelation-preventive property is exhibited. Where the total is above 70, the hydrophilic property thereof becomes so strong that its conditioning effect is rendered insufficient, although gelation of the composition can be prevented. Preferably, $a_1$, $a_2$ and $a_3$ are each 0. In other words, it is preferred that the polyol derivatives do not have any propylene oxide units since the gelation-preventive property may be enhanced. In this case, the total sum of $b_1+b_2+b_3$ ranges from 10 to 70. Also, the gelation-preventive property may be further enhanced if the higher aliphatic acid residue or the higher hydroxyaliphatic acid residue has 12 to 24 carbon atoms.

In the formula (V), each of $m_1$, $m_2$, $m_3$, $m_4$, $m_5$, $m_6$, $n_1$, $n_2$, $n_3$, $n_4$, $n_5$ and $n_6$ is an integer and a total number of $m_1+m_2+m_3+m_4+m_5+m_6+n_1+n_2+n_3+n_4+n_5+n_6$ is between 10 and 100. Where the total is below 10, a hydrophilic property of the composition becomes too low to prevent gelation. Where the total is above 100, the hydrophilic property of the composition becomes too strong and the conditioning effect becomes insufficient, although gelation is prevented. Preferably, $n_1$, $n_2$, $n_3$, $n_4$, $n_5$ and $n_6$ are each 0. In other words, it is preferred that the polyol derivatives do not have any propylene oxide units since the gelation-preventive property may be enhanced. In this case, the total sum of $m_1+m_2+m_3+m_4+m_5+m_6$ ranges from 10 to 100. Also, the gelation-preventive property may be further enhanced if the higher aliphatic acid residue or the higher hydroxyaliphatic acid residue has 12 to 24 carbon atoms.

The hair cosmetic composition according to the present invention contains at least one polyol derivative represented by the general formula (III), (IV) or (V) in an amount ranging from about 0.05 to about 20% by weight. Where the amount of the polyol derivative is below about 0.05% by weight, gelation of the composition cannot be prevented. Where the amount thereof exceeds about 20% by weight, its conditioning effect is reduced.

The polyol derivatives represented by the general formula (III), (IV) and (V) per se are known in the art and can be manufactured by the process disclosed in Japanese Patent Disclosure (Kokai) No. 110,584/74. To be brief, a polyoxyalkylenepolyolmonopyrrolidone carbonate monoaliphatic acid ester may be manufactured by the process as follows: Equimolar of a polyoxyalkylenepolyol ether, an aliphatic acid and pyrrolidone carboxylic acid are mixed with a 10 to 50% (based on the total volume of the above three starting materials) of a non-polar solvent such as toluene, xylene or the like in a reaction vessel. After extensive stirring, an acid catalyst is added to the reaction mixture and the reaction mixture is kept at a temperature of 100° to 200° C. for 1 to 10 hours while continuously stirring. In this reaction, water should be removed as much as possible to promote the reaction rate. Other polyol derivatives may be manufactured by the similar process by varying the starting materials and their amounts.

In the description of the specification which follows, term EO means the average number of ethylene oxide units, and term PO means the average number of propylene oxide units. Use of the term 20 EO, for example, means that an average number of ethylene oxide units in a molecule is 20. Terms POE and POP denote abbreviations of polyoxyethylene and polyoxypropylene, respectively.

Specific examples of the polyol derivatives of formula (III) include POE monopyroglutamate monoisostearate glycerin (25 EO), POE monopyroglutamate monooleate glycerin (30 EO), POE POP dipyroglutamate monostearate glycerin (25 EO; 10 PO), POE monopyroglutamate monolinolate glycerin (25 EO), POE POP monopyroglutamate monolinoleate glycerin (15 EO; 15 PO), POE monopyroglutamate monoricinoleate glycerin (30 EO), POE monopyroglutamate monoerucate glycerin (35 EO), POE POP tripyroglutamate glycerin (15 EO, 5 PO) and POE POP monopyroglutamate monobehenate glycerin (10 EO, 20 PO).

Specific examples of the polyol derivatives represented by formula (IV) includes POE monopyroglutamate monoisostearate hardened castor oil (40 EO), POE monopyroglutamate monooleate hardened castor oil (30 EO), POE monopyroglutamate monoerucate hardened castor oil (45 EO), POE monopyroglutamate monolinoleate hardened castor oil (35 EO), POE monopyroglutamate monoricinoleate hardened castor oil (50 EO), POE POP dipyroglutamate monopalmitate hardened castor oil (35 EO, 5 PO), POE POP dipyroglutamate monobehenate hardened castor oil (15 EO, 15 PO), POE POP tripyroglutamate hardened castor oil (10 EO, 25 PO), POE tripyroglutamate hardened castor oil (50 EO) and POE POP dipyroglutamate monopalmitate hardened castor oil (35 EO, 5 PO).

Specific examples of the polyol derivatives represented by general formula (V) includes POE monopyroglutamate triisostearate sorbitol (50 EO), POE monopyroglutamate trioleate sorbitol (60 EO), POE monopyroglutamate monooleate sorbitol (70 EO), POE monopyroglutamate monostearate sorbitol (55 EO), POE monopyroglutamate dilinolate sorbitol (40 EO, 10 PO), POE monopyroglutamate monoricinoleate sorbital (45 EO), POE POP dipyroglutamate dioleate sorbitol (40 EO, 10 PO), POE POP dipyroglutamate diisostearate sorbitol (35 EO, 20 PO), POE POP dipyroglutamate monoricinoleate sorbitol (40 EO, 10 PO), POE tripyroglutamate monoisostearate sorbitol (50 EO), POE POP tripyroglutamate monooleate sorbitol (50 EO, 5 PO), POE tetrapyroglutamate sorbitol (60 EO), and POE POP tetrapyroglutamate sorbitol (40 EO, 20 PO).

The hair cosmetic composition according to the present invention contains a cosmetically acceptable carrier in addition to the ingredients set forth above. The carrier is well known in the pertinent art so that it is deemed unnecessary to describe details of such carriers here. Appropriate carriers includes, for example, water; ethanol; polyol such as ethylene glycol, propylene glycol, 1,3-butylene glycol, glycerin and sorbitol; siloxane such as dimethyl polysiloxane, phenyl polysiloxane and polyoxyalkylene polysiloxane; animal or plant oil such as sperm oil and zozoba oil; liquid paraffin; vaseline; paraffin wax; squalane and an olefin oligomer.

The hair cosmetic composition according to the present invention may contain the following ingredients in an arbitrary manner in any amount without affecting the effects provided by the composition according to the present invention. The ingredients may include, for example, an ester capable of providing hair with further pliability, such as isopropyl myristate, isopropyl palmitate, stearyl stearate, octyldodecyl myristate, octyldodecyl oleate and 2-ethylhexanoic acid triglyceride; an emulsifier such as polyoxyethylenecetyl ether, polyoxyethylenestearic acid ester and polyoxyethylenesorbitan monolaurate; an emulsifier such as, sorbitan monopalmitate, polyoxyethylenecetyl ether, polyoxyethylenestearic acid ester and polyoxyethylene sorbitan monolaurate; a material capable of enhancing adsorption onto hair, such as a cellulose derivative, e.g., methylcellulose, hydroxyethyl cellulose, hydroxypropyl cellulose and cationated cellulose; a thickening agent such as a natural polymer; and minute amounts of ingredients such as other solvents, fungicides and perfume.

The hair cosmetic composition according to the present invention may be in a form of a hair rinse composition, a hair conditioner composition, a hair treatment composition, a hair cream composition, a hair lotion composition and any other hair cosmetic composition.

The present invention will be described in more detail by way of working examples and comparative examples. In the examples which follow, amounts are expressed as % by weight.

The following is an explanation of methods of testing the performance of compositions and of rating such performance.

A. Method of Testing Gelation-Prevention

A sample hair cosmetic composition was prepared by heating ingredients other than water to 70° C., adding this to water at 72° C. with stirring, emulsifying the mixture, and aging. The aged emulsion was then cooled to 25° C. and measured for viscosity (hereinafter referred to as "first viscosity"). The sample was then stored at room temperature for one month and measured again for viscosity (hereinafter referred to as "second viscosity").

Measurement of viscosity was carried out with a BL type viscometer. The viscosity was measured by rotating a Rotor No. 3 at a rate of 30 r.p.m. at 25° C., and observing the viscosity after the 10th rotation.

Performance Evaluation Ratings

Very Good: A difference between first and second viscosities is within ±100 centipoises.

Good: A difference between first and second viscosities is within ±200 centipoises.

Bad: A difference between first and second viscosities exceeds ±200 centipoises.

B. Method of Testing Conditioning Effect

Onto a shampoo-treated hair bundle (5 g, 20 cm), 0.5 g of sample composition was directly applied and was manually extended uniformly. The hair bundle was then dried in the atmosphere of 65% RH at 25° C. for 24 hours. After such treatment, the combing easiness, the softness, the smoothness and the moisture of the hair bundle were evaluated by 20 persons. The evaluation was conducted by the sense or feeling of the persons without using any measurement device. The above four factors are collectively referred to as "conditioning effect" in Table 1.

As a control, the same procedure was conducted using a control composition consisting of 1.0% by weight of stearyltrimethylammonium chloride, 3% by weight of cetyl alcohol, 10% by weight of propylene glycol and water (balance).

Performance Evaluation Ratings
S: Superior to the control
LS: Little superior to the control
E: Equivalent to the control thylpentyl)-2-pyridone.monoethanolamine having the following structural formula:

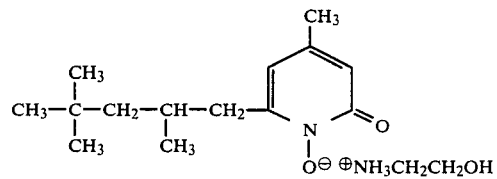

TABLE 1

| Examples | 1 | | | | | | | | 2 | 3 | 4 | 5 | 6 | 7 |
| Comparative Examples | | 1 | 2 | 3 | 4 | 5 | 6 | 7 | | | | | | |
| Ingredients (% by weight) | | | | | | | | | | | | | | |
|---|---|---|---|---|---|---|---|---|---|---|---|---|---|---|
| Pyrocutonolamine* | 0.3 | 0.3 | 0.3 | 0.3 | 0.3 | 0.3 | 0.3 | 0.3 | 0.3 | 0.3 | 0.3 | 0.3 | 0.3 | 0.3 |
| POE (25) monopyroglutamate monoisostearate glycerin | 0.5 | | | | | | | | | | | | | |
| POE (25) monoisostearate glycerin | | 0.5 | | | | | | | | | | | | |
| POE (25) triisostearate glycerin | | | 0.5 | | | | | | | | | | | |
| POE (20) monolaurate sorbitan | | | | 0.5 | | | | | | | | | | |
| POE (20) monostearate sorbitan | | | | | 0.5 | | | | | | | | | |
| POE (20) monopalmitate sorbitan | | | | | | 0.5 | | | | | | | | |
| POE (25) monostearic acid ester | | | | | | | 0.5 | | | | | | | |
| POE (20) stearyl alcohol ether | | | | | | | | 0.5 | | | | | | |
| POE (20) monopyroglutamate monoisostearate glycerin | | | | | | | | | 0.3 | 0.1 | | | | |
| POE (40) monopyroglutamate monoisostearate hardened castor oil | | | | | | | | | | 0.2 | | | | |
| POE (30) tetrapyroglutamate sorbitol | | | | | | | | | | | 0.5 | | | |
| POP (5) POE (15) monopyroglutamate monolaurate glycerin | | | | | | | | | | | | 0.6 | | |
| POP (10) POE (40) monopyroglutamate monopalmitate hardened castor oil | | | | | | | | | | | | | 1.0 | |
| POP (3) POE (20) dipyroglutamate dioleate sorbitol | | | | | | | | | | | | | | 0.5 |
| Liquid paraffin (70 seconds) | 0.5 | 0.5 | 0.5 | 0.5 | 0.5 | 0.5 | 0.5 | 0.5 | 0.5 | 0.5 | 0.5 | 0.5 | 0.5 | 0.5 |
| Cetyl alcohol | 3.0 | 3.0 | 3.0 | 3.0 | 3.0 | 3.0 | 3.0 | 3.0 | 1.0 | 1.0 | 1.0 | 1.0 | 1.0 | 1.0 |
| POE (10) stearyl ether | 2.0 | 2.0 | 2.0 | 2.0 | 2.0 | 2.0 | 2.0 | 2.0 | 2.0 | 2.0 | 2.0 | 2.0 | 2.0 | 2.0 |
| Propylene glycol | 5.0 | 5.0 | 5.0 | 5.0 | 5.0 | 5.0 | 5.0 | 5.0 | 3.0 | 3.0 | 3.0 | 3.0 | 3.0 | 3.0 |
| Dimethyl distearyl ammonium chloride | | | | | | | | | 2.0 | 2.0 | 2.0 | 2.0 | 2.0 | 2.0 |
| Stearyl trimethyl ammonium chloride | 1.0 | 1.0 | 1.0 | 1.0 | 1.0 | 1.0 | 1.0 | 1.0 | | | | | | |
| Purified water | balance | balance | balance | balance | balance | balance | balance | balance | balance | balance | balance | balance | balance | balance |
| Prevention of gelation | very good | bad | bad | bad | bad | bad | bad | bad | very good | very good | good | good | good | good |
| First viscosity (CP/25° C.) | 1540 | 760 | 1600 | 720 | 1800 | 1040 | 800 | 1960 | 1740 | 2200 | 1100 | 1830 | 1080 | 1340 |
| Second viscosity (CP/25° C.) | 1620 | 1060 | 2800 | 1100 | 2200 | 1620 | 1550 | 2900 | 1820 | 2300 | 930 | 2020 | 1250 | 1500 |
| Conditioning effect | S | E | E | E | E | E | E | E | LS | LS | LS | LS | LS | LS |

LI: Little inferior to the control
I: Inferior to the control

Test 1

Compositions having ingredients shown in Table 1 below were prepared and tested for their performance according to the test methods mentioned hereinabove. In Table 1 below, the pyrocutonolamine indicated by the asterisk (*) is 1-hydroxy-4-methyl-6-(2,4,4-trimethylpentyl)-2-pyridone.monoethanolamine It is found from the test results shown in Table 1 above that the compositions as illustrated in the Comparative Examples containing no polyol derivatives represented by formula (III), (IV) or (V) have a large variation between first and second viscosities above 200 centipoises so that gelation is poorly prevented. The compositions according to the present invention as shown in Examples 1 to 7, inclusive, exhibit only a small variation between first and second viscosities so that little gelation is allowed. The compositions of the present invention also have better conditioning effect than those of Comparative Examples.

EXAMPLE 8

A hair treatment composition having the ingredients shown in Table 2 below was prepared for measuring the performance thereof.

TABLE 2

| Composition | Amount |
|---|---|
| Quaternary ammonium salt *1 | 1.0 |
| POE (20) monopyroglutamate monoisostearate glycerin | 1.0 |
| 1-hydroxy-2-pyridone salt *2 | 0.5 |
| Liquid paraffin (70 seconds) | 15 |
| Cetanol | 3.5 |
| Stearic acid | 0.5 |
| Sorbitan monopalmitate | 1.5 |
| POE (15) stearyl ether | 0.7 |
| Propylene glycol | 5.0 |
| Purified water | Balance |

This hair treatment composition had a high conditioning effect and allowed little gelation.

EXAMPLE 9

A hair lotion composition having the ingredients shown in Table 3 below was prepared for measuring the performance thereof.

TABLE 3

| Composition | Amount |
|---|---|
| Quaternary ammonium salt *3 | 0.5 |
| POP (5) POE (25) monopyroglutamate monolaurate glycerin | 0.5 |
| 1-hydroxy-2-pyridone salt *4 | 0.3 |
| Cetanol | 2.0 |
| Squalane | 5 |
| Glycerin monostearate | 1.0 |
| POE (10) stearyl ether | 0.8 |
| Propylene glycol | 5.0 |
| Purified water | Balance |

This hair lotion composition was found to have a strong conditioning effect and to allow little gelation.

In Tables 2 and 3 above, the compounds indicated by the asterisk (*) and numerals have the following structural formulas:

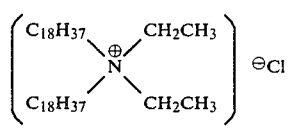

*1

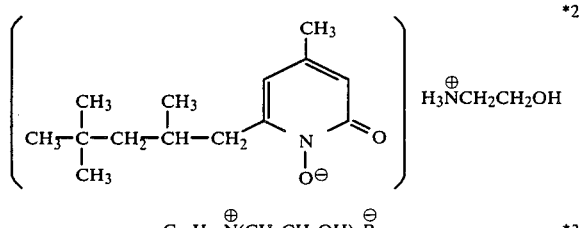

*2

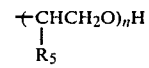

*3

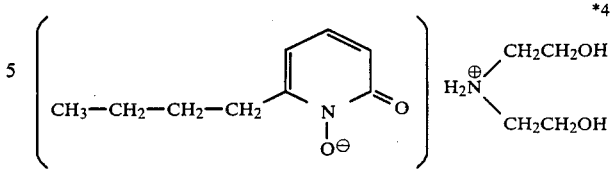

*4

What we claim is:

1. A hair conditioning composition which provides a strong conditioning effect and substantially no gelation comprising:
   (A) at least one quaternary ammonium salt represented by formula (I) in an amount ranging from about 0.1 to about 10% by weight;
   (B) at least one 1-hydroxy-2-pyridone salt represented by formula (II) in an amount ranging from about 0.05 to about 3.0% by weight;
   (C) at least one polyol derivative represented by formula (III), (IV) or (V) in an amount ranging from about 0.05 to about 20% by weight; and
   (D) a cosmetically acceptable carrier; wherein said formula (I) is:

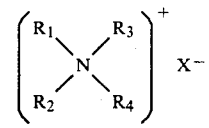

where $R_1$ is a $C_{10}$–$C_{24}$ alkyl group, a $C_{10}$–$C_{24}$ hydroxyalkyl group, or a group having the formula $R'(OCH_2CH_2-)_{1-10}$, where $R'$ is a $C_{10}$–$C_{24}$ alkyl group or a $C_{10}$–$C_{24}$ hydroxyalkyl group; $R_2$ is a $C_{10}$–$C_{24}$ alkyl group, a $C_{10}$–$C_{24}$ hydroxyalkyl group, benzyl group, a group having the formula $R''(OCH_2CH_2)_{1-10}$ where $R''$ is a $C_{10}$–$C_{24}$ alkyl group or a $C_{10}$–$C_{24}$ hydroxyalkyl group, a $C_1$–$C_3$ alkyl group, or a group having the formula $$+CHCH_2O)_nH \atop R_5$$

where n is an integer from 1 to 5 and $R_5$ is a hydrogen atom or methyl group; $R_3$ and $R_4$ are independently a $C_1$–$C_3$ alkyl group or a group having the formula $$+CHCH_2O)_mH, \atop R_6$$

where m is an integer from 1 to 5 and $R_6$ is a hydrogen atom or methyl group; and X is a halogen atom or a $C_1$–$C_2$ alkyl sulfate group;
said formula (II) is:

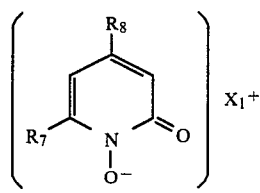

where $R_7$ is a $C_1$-$C_{17}$ alkyl group, a $C_2$-$C_{17}$ alkenyl group, a $C_5$-$C_8$ cyclcoalkyl group, a $C_7$-$C_9$ bicycloalkyl group, a $C_1$-$C_4$ cycloalkyl-alkyl group where the cycloalkyl residue may optionally be substituted by a $C_1$-$C_4$ alkyl group, an aryl group, an aralkyl group containing a $C_1$-$C_4$ alkyl group, an arylalkenyl group containing a $C_2$-$C_4$ alkenyl group, an aryloxyalkyl group containing a $C_1$-$C_4$ alkyl group, an arylmercaptoalkyl group containing a $C_1$-$C_4$ alkyl group, a benzhydryl group, a phenylsulfonylalkyl group containing a $C_1$-$C_4$ alkyl group, a furyl group, or a furylalkenyl group containing a $C_2$-$C_4$ alkenyl group, provided that said aryl residue may optionally be substituted by a $C_1$-$C_4$ alkyl group, a $C_1$-$C_4$ alkoxy group, nitro group, cyano group or a halogen atom;

$R_8$ is a hydrogen atom, a $C_1$-$C_4$ alkyl group, a $C_2$-$C_4$ alkenyl group, a $C_2$-$C_4$ alkynyl group, a halogen atom, a phenyl group or a benzyl group; and $X_1$ is an organic base, an alkali metal, an alkaline earth metal, ammonium group, or a cation of +2 to +4 valence;

said formula (III) is:

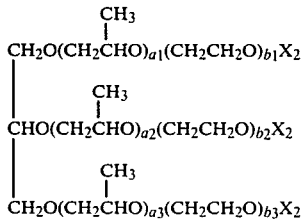

where at least one of $X_2$ is a pyrrolidone carboxylic acid residue and the remaining $X_2$ are each independently a hydrogen atom, a higher aliphatic acid residue or a higher hydroxylaliphatic acid residue; $a_1$, $a_2$, $a_3$, $b_1$, $b_2$ and $b_3$ are the same or different integers and a total sum of $a_1+a_2+a_3+b_1+b_2+b_3$ is an integer between 10 and 70;

said formula (IV) is:

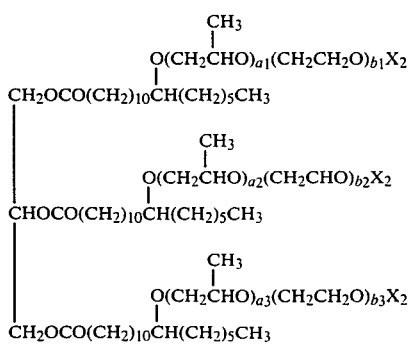

where $X_2$, $a_1$, $a_2$, $a_3$, $b_1$, $b_2$ and $b_3$ have the same meaning as in formula (III); and said formula (V) is:

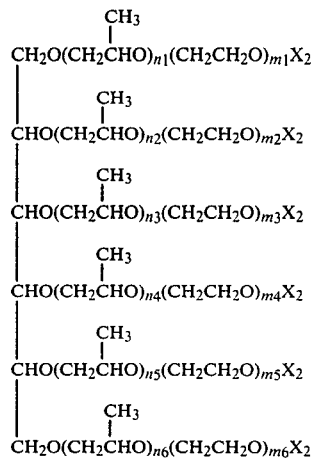

where $X_2$ has the same meaning as in formula (III) above; $m_1$, $m_2$, $m_3$, $m_4$, $m_5$, $m_6$, $n_1$, $n_2$, $n_3$, $n_4$, $n_5$ and $n_6$ are the same or different integers and a total sum of $m_1+m_2+m_3+m_4+m_5+m_6+n_1+n_2+n_3+n_4+n_5+n_6$ is an integer between 10 and 100.

2. The composition according to claim 1, wherein said $R_1$ is a $C_{12}$-$C_{22}$ alkyl group, a $C_{12}$-$C_{22}$ hydroxyalkyl group, or a group having the general formula $R'(OCH_2CH_2)_{1-10}$ (where $R'$ is a $C_{12}$-$C_{22}$ alkyl group or a $C_{12}$-$C_{12}$ hydroxyalkyl group); said $R_2$ is a $C_{12}$-$C_{22}$ alkyl group, a $C_{12}$-$C_{22}$ hydroxyalkyl group, benzyl group, $R''(OCH_2CH_2)_{1-10}$ (where $R''$ is a $C_{12}$-$C_{22}$ alkyl group or a $C_{12}$-$C_{22}$ hydroxyalkyl group), $C_1$-$C_2$ alkyl group or a group having the formula

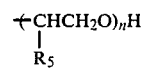

where $n$ is an integer from 1 to 5 and $R_5$ is hydrogen atom or methyl group); and said $R_3$ and said $R_4$ are independently a $C_1$-$C_2$ alkyl group or a group having the formula

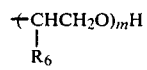

(where $m$ is an integer from 1 to 5 and $R_6$ is hydrogen atom or methyl group).

3. The composition according to claim 1, wherein said 1-hydroxy-2-pyridone salt is the organic amine salt of:

1-hydroxy-2-pyridone, 1-hydroxy-4-methyl-2-pyridone, 1-hydroxy-6-methyl-2-pyridone, 1-hydroxy-4,6-dimethyl-2-pyridone, 1-hydroxy-4-methyl-6-heptyl-2-pyridone, 1-hydroxy-4-methyl-6-(1-ethyl-pentyl)-2-pyridone, 1-hydroxy-4-methyl-6-(2,4,4-trimethyl-pentyl)-2-pyridone, 1-hydroxy-4-methyl-6-undecyl-2-pyridone, 1-hydroxy-4-methyl-6-propenyl-2-pyridone, 1-hydroxy-4-methyl-6-octenyl-2-pyridone, 1-hydroxy-4-methyl-6-(2,2-dibutyl-vinyl)-2-pyridone,
1-hydroxy-4-methyl-6-(cyclohexenylidene-methyl)-2-pyridone,
1-hydroxy-4-methyl-6-cyclohexyl-2-pyridone,
1-hydroxy-4-methyl-6-(methyl-cyclohexyl)-2-pyridone,
1-hydroxy-4-methyl-6-(2-bicyclo[2,2,1]heptyl)-2-pyridone,
1-hydroxy-4-methyl-6-[-2-(dimethylcyclohexyl)-propyl]-2-pyridone,
1-hydroxy-4-methyl-6-(4-methyl-phenyl-)-2-pyridone,
1-hydroxy-4-methyl-6-(3-methyl-phenyl-)-2-pyridone,
1-hydroxy-4-methyl-6-(4-tert.-butyl-phenyl)-2-pyridone,
1-hydroxy-4-methyl-6-(3-methyl-4-chloro-phenyl)-2-pyridone,
1-hydroxy-4-methyl-6-(3,5-dichloro-phenyl)-2-pyridone,
1-hydroxy-4-methyl-6-(3-bromo-4-chloro-phenyl)-2-pyridone,
1-hydroxy-4-methyl-6-(4-methoxystyryl)-2-pyridone,
1-hydroxy-4-methyl-6-[-(4-nitrophenoxy)-butyl]-2-pyridone,
1-hydroxy-4-methyl-6-(4-cyanophenoxymethyl)-2-pyridone,
1-hydroxy-4-methyl-6-(phenylsulfonylmethyl)-2-pyridone,
1-hydroxy-4-methyl-6-[1-chlorophenylsulfonyl)-butyl]-2-pyridone,
1-hydroxy-4-methyl-6-benzyl-2-pyridone,
1-hydroxy-4-methyl-6-(2,4-dimethyl-benzyl)-2-pyridone,
1-hydroxy-4-methyl-6-(tert.-butyl-benzyl)-2-pyridone,
1-hydroxy-4-methyl-6-(2-chloro-benzyl)-2-pyridone,
1-hydroxy-4-methyl-6-(4-chloro-benzyl)-2-pyridone,
1-hydroxy-4-methyl-6-(2,5-dichloro-benzyl)-2-pyridone,
1-hydroxy-4-methyl-6-(4-bromo-benzyl)-2-pyridone,
1-hydroxy-4-methyl-6-(phenoxymethyl)-2-pyridone,
1-hydroxy-4-methyl-6-(3-methylphenoxy-methyl)-2-pyridone,
1-hydroxy-4-methyl-6-(4-sec.-butylphenoxy-methyl)-2-pyridone,
1-hydroxy-4-methyl-6-(2,4,5-trichlorophenoxymethyl)-2-pyridone,
1-hydroxy-4-methyl-6-(4-bromophenoxy-methyl)-2-pyridone,
1-hydroxy-4-methyl-6-(4-chlorophenylthio-methyl)-2-pyridone,
1-hydroxy-4-methyl-6-(4-methylphenylthio-methyl)-2-pyridone,
1-hydroxy-4-methyl-6-(2-naphthyl)-2-pyridone,
1-hydroxy-4-methyl-6-benzhydryl-2-pyridone,
1-hydroxy-4-methyl-6-furyl-2-pyridone,
1-hydroxy-4-methyl-6-(furylvinyl)-2-pyridone,
1-hydroxy-4-methyl-6-styryl-2-pyridone,
1-hydroxy-4-methyl-6-(phenylbutadienyl)-2-pyridone,
1-hydroxy-4-phenyl-6-methyl-2-pyridone, or
1-hydroxy-4,6-diphenyl-2-pyridone.

4. The composition according to claim 1, wherein, in said formula (III), said $a_1$, $a_2$ and $a_3$ are each 0 and a total sum of $b_1+b_2+b_3$ is an integer between 10 and 70, said higher aliphatic acid residue has 12 to 24 carbon atoms, and said higher hydroxylaliphatic acid residue has 12 to 24 carbon atoms.

5. The composition according to claim 1, wherein, in said formula (IV), said $a_1$, $a_2$ and $a_3$ are each 0 and a total sum of $b_1+b_2+b_3$ is an integer between 10 and 70, said higher aliphatic acid residue has 12 to 24 carbon atoms, and said higher hydroxylaliphatic acid residue has 12 to 24 carbon atoms.

6. The composition according to claim 1, wherein, in said formula (V), said $n_1$, $n_2$, $n_3$, $n_4$, $n_5$ and $n_6$ are each 0 and a total sum of $m_1+m_2+m_3+m_4+m_5+m_6$ is an integer between 10 and 100, said higher aliphatic acid residue has 12 to 24 carbon atoms, and said higher hydroxyaliphatic acid residue has 12 to 24 carbon atoms.

7. The composition according to claim 1, wherein said quaternary ammonium salt is dimethyldistearylammonium chloride, stearyltrimethylammonium chloride, diethyldistearylammonium chloride or behenyltriethanolammonium bromide.

8. The composition according to claim 1, wherein said 1-hydroxy-2-pyridone salt is 1-hydroxy-4-methyl-6-(2,4,4-trimethylpentyl)-2pyridone.monoethanolamine or 1-hydroxy-6-n-butyl-2-pyridone.diethanolamine.

9. The composition according to claim 1, wherein said polyol derivative represented by the formula (III) is monopyroglutamatemonoisostearatepolyoxyethylene glycerin (20 EO) or monopyroglutamatemonolauratepolyoxyethylenepolyoxypropylene glycerin (15 EO, 5 PO).

10. The composition according to claim 1, wherein said polyol derivative represented by the formula (IV) is monopyroglutamatemonoisostearatepolyoxyethylene hardened castor oil (40 EO) or monopyroglutamatemonopalmitatepolyoxyethylenepolyoxypropylene hardened castor oil (40 EO, 10 PO).

11. The composition according to claim 6, wherein said polyol derivative represented by the formula (V) is tetrapyroglutamatepolyoxyethylene sorbitol (30 EO) or dipyroglutamatedioleatepolyoxyethylenepolyoxypropylene sorbitol (20 EO, 3 PO).

* * * * *